United States Patent
Holm et al.

(10) Patent No.: US 12,156,516 B2
(45) Date of Patent: Dec. 3, 2024

(54) METHOD FOR OPTIMIZATION OF FILTRATION IN AN AQUACULTURE SYSTEM

(71) Applicants: Thue Holm, Vejle (DK); Julian Fiorentino, Miami, FL (US)

(72) Inventors: Thue Holm, Vejle (DK); Julian Fiorentino, Miami, FL (US)

(73) Assignee: ATLANTIC SAPPHIRE IP, LLC, Homestead, FL (US)

( * ) Notice: Subject to any disclaimer, the term of this patent is extended or adjusted under 35 U.S.C. 154(b) by 123 days.

(21) Appl. No.: 17/899,349

(22) Filed: Aug. 30, 2022

(65) Prior Publication Data

US 2023/0079755 A1 Mar. 16, 2023

Related U.S. Application Data

(63) Continuation of application No. 17/079,007, filed on Oct. 23, 2020, now Pat. No. 11,425,895, which is a
(Continued)

(51) Int. Cl.
*A01K 63/04* (2006.01)
*C02F 1/32* (2023.01)
(Continued)

(52) U.S. Cl.
CPC .............. *A01K 63/045* (2013.01); *C02F 1/68* (2013.01); *C02F 3/006* (2013.01); *C02F 3/02* (2013.01);
(Continued)

(58) Field of Classification Search
CPC ......... A01K 63/045; C02F 1/68; C02F 3/006; C02F 3/02; C02F 1/32; C02F 3/043;
(Continued)

(56) References Cited

U.S. PATENT DOCUMENTS

| | | | |
|---|---|---|---|
| 2,643,481 | A | 6/1953 | Ederer |
| 3,200,949 | A | 8/1965 | Aulich |

(Continued)

FOREIGN PATENT DOCUMENTS

| | | |
|---|---|---|
| CA | 2711677 | 11/2012 |
| CN | 102329055 | 1/2012 |

(Continued)

OTHER PUBLICATIONS

Jonns et al., Streptophage-Mediated Control of Off-Flavour Taint Producing Streptomycetes Isolated From Barramundi Ponds, Apr. 12, 2017.

(Continued)

*Primary Examiner* — Fred Prince
(74) *Attorney, Agent, or Firm* — MALLOY & MALLOY, PL

(57) ABSTRACT

A method for optimizing filtration in an aquaculture system. The method for optimizing filtration includes, taking at least one sample of matter from an aquaculture system, defining at least one predetermined characteristic to test the sample of matter for, testing the at least one sample of matter, determining if the at least one predetermined characteristic is present within the sample, modifying resource distribution within the aquaculture system, taking at least two samples of matter within the aquaculture system, re-defining at least one predetermined characteristic to test the at least two samples of matter for, testing the at least two samples of matter, determining if the re-defined at least one predetermined characteristic is present within the at least two samples of matter and ensuring the filtration system will retain a state of optimization.

19 Claims, 1 Drawing Sheet

Related U.S. Application Data continuation-in-part of application No. 16/992,865, filed on Aug. 13, 2020, which is a continuation-in-part of application No. 16/992,760, filed on Aug. 13, 2020, which is a continuation-in-part of application No. 16/991,162, filed on Aug. 12, 2020, now abandoned.

(60) Provisional application No. 62/985,592, filed on Mar. 5, 2020.

(51) Int. Cl.
    *C02F 1/68* (2023.01)
    *C02F 3/00* (2023.01)
    *C02F 3/02* (2023.01)
    *C02F 3/04* (2023.01)
    *G01N 31/22* (2006.01)
    *G01N 33/18* (2006.01)
    *C02F 103/20* (2006.01)

(52) U.S. Cl.
    CPC ............ *G01N 31/22* (2013.01); *G01N 33/18* (2013.01); *C02F 1/32* (2013.01); *C02F 3/043* (2013.01); *C02F 2103/20* (2013.01); *C02F 2209/06* (2013.01); *C02F 2209/14* (2013.01); *C02F 2209/15* (2013.01); *C02F 2301/046* (2013.01)

(58) Field of Classification Search
    CPC ............ C02F 2103/20; C02F 2209/06; C02F 2209/14; C02F 2209/15; C02F 2301/046; G01N 31/22; G01N 33/18
    USPC .......... 210/614, 615, 616, 617, 167.21, 903; 119/226, 227, 260
    See application file for complete search history.

(56) References Cited

U.S. PATENT DOCUMENTS

| | | |
|---|---|---|
| 3,771,492 A | 11/1973 | Doherty |
| 3,832,720 A | 8/1974 | Cook |
| 4,009,782 A | 3/1977 | Grimshaw |
| 4,052,960 A | 10/1977 | Birkbeck et al. |
| 4,067,809 A | 1/1978 | Kato |
| 4,141,318 A | 2/1979 | MacVane et al. |
| 4,225,543 A | 9/1980 | Hohman |
| 4,394,259 A | 7/1983 | Benny et al. |
| 4,607,595 A | 8/1986 | Busot et al. |
| 4,728,438 A | 3/1988 | Featherstone et al. |
| 4,915,059 A | 4/1990 | Long |
| 4,966,096 A | 10/1990 | Adey |
| 5,038,715 A | 8/1991 | Fahs, II |
| 5,123,195 A | 6/1992 | Hawkins |
| 5,186,121 A | 2/1993 | Smith, Jr. |
| 5,317,645 A | 5/1994 | Perozek et al. |
| 5,385,428 A | 1/1995 | Taft, 3rd et al. |
| 5,540,521 A | 7/1996 | Biggs |
| 5,659,977 A | 8/1997 | Jensen et al. |
| 5,732,654 A | 3/1998 | Perez et al. |
| 5,823,142 A | 10/1998 | Cardinale et al. |
| 5,961,831 A | 10/1999 | Lee et al. |
| 5,978,315 A | 11/1999 | Molaug |
| 5,979,362 A | 11/1999 | McRobet |
| 6,000,362 A | 12/1999 | Blyth et al. |
| 6,041,738 A | 3/2000 | Hemauer et al. |
| 6,065,430 A | 5/2000 | Sheriff |
| 6,099,879 A | 8/2000 | Todd, Jr. |
| 6,206,612 B1 | 3/2001 | Meyer |
| 6,317,385 B1 | 11/2001 | Hedgepeth |
| 6,382,134 B1 | 5/2002 | Gruenberg et al. |
| 6,443,098 B1 | 9/2002 | Blyth et al. |
| 6,447,681 B1 | 9/2002 | Carlberg et al. |
| 6,474,264 B1 | 11/2002 | Grimberg et al. |
| 6,499,431 B1 | 12/2002 | Lin et al. |
| 6,722,314 B1 | 4/2004 | Crisinel et al. |
| 6,902,675 B2 | 6/2005 | Kelly et al. |
| 6,932,025 B2 | 8/2005 | Massingill et al. |
| 6,986,323 B2 | 1/2006 | Ayers |
| 6,988,394 B2 | 1/2006 | Shedd et al. |
| 7,001,519 B2 | 2/2006 | Linden et al. |
| 7,082,893 B2 | 8/2006 | Schreier et al. |
| 7,462,284 B2 | 12/2008 | Schreier et al. |
| 7,594,779 B2 | 9/2009 | Hildstad et al. |
| 7,736,509 B2 * | 6/2010 | Kruse .................... C02F 3/348 210/906 |
| 8,117,992 B2 | 2/2012 | Parsons et al. |
| 8,141,515 B2 | 3/2012 | Nien |
| 8,506,811 B2 | 8/2013 | Bradley et al. |
| 8,535,883 B2 | 9/2013 | Cane et al. |
| 8,633,011 B2 | 1/2014 | Palmer et al. |
| 9,637,402 B2 | 5/2017 | Tal et al. |
| 9,756,838 B2 | 9/2017 | Kunitomo et al. |
| 10,034,461 B2 | 7/2018 | Holm et al. |
| 10,131,558 B1 * | 11/2018 | Cox, Jr. .................. C02F 1/683 |
| 10,338,631 B1 | 7/2019 | Jorden et al. |
| 10,660,315 B1 | 5/2020 | Alcantar et al. |
| 10,694,722 B1 | 6/2020 | Holm et al. |
| 10,748,278 B2 | 8/2020 | Brubacher |
| 10,959,411 B2 | 3/2021 | Holm |
| 11,425,895 B2 | 8/2022 | Holm et al. |
| 11,484,015 B2 | 11/2022 | Holm et al. |
| 11,596,132 B2 | 3/2023 | Holm |
| 11,627,729 B2 | 4/2023 | Holm et al. |
| 11,662,291 B1 | 5/2023 | Holm |
| 11,785,921 B2 | 10/2023 | Holm |
| 2003/0059494 A1 | 3/2003 | Ang et al. |
| 2003/0070624 A1 | 4/2003 | Zohar et al. |
| 2003/0104353 A1 | 6/2003 | Brielmeier et al. |
| 2003/0121859 A1 | 7/2003 | Kelly et al. |
| 2004/0168648 A1 | 9/2004 | Ayers |
| 2004/0244715 A1 | 12/2004 | Schreier et al. |
| 2005/0211644 A1 | 9/2005 | Goldman |
| 2006/0055934 A1 | 3/2006 | Sunshine et al. |
| 2007/0221552 A1 | 9/2007 | Denney |
| 2007/0242134 A1 | 10/2007 | Zernov |
| 2008/0000821 A1 | 1/2008 | Drewelow |
| 2008/0223788 A1 | 9/2008 | Rimdzius et al. |
| 2009/0145368 A1 | 6/2009 | Brauman |
| 2009/0250010 A1 | 10/2009 | Urusova et al. |
| 2010/0081961 A1 | 4/2010 | Cox |
| 2010/0092431 A1 | 4/2010 | Liles et al. |
| 2010/0236137 A1 | 9/2010 | Wu et al. |
| 2010/0269761 A1 | 10/2010 | Nien |
| 2011/0046603 A1 | 2/2011 | Felsovalyi et al. |
| 2011/0168616 A1 * | 7/2011 | Robertson ............... C02F 3/302 210/141 |
| 2011/0250604 A1 | 10/2011 | Cane et al. |
| 2011/0258915 A1 | 10/2011 | Subhadra |
| 2012/0103271 A1 | 5/2012 | Kong |
| 2012/0125940 A1 | 5/2012 | Wright et al. |
| 2012/0184001 A1 | 7/2012 | Stephen et al. |
| 2013/0098303 A1 | 4/2013 | Jones |
| 2013/0273599 A1 | 10/2013 | Robitaille et al. |
| 2013/0319342 A1 | 12/2013 | Musser |
| 2013/0327709 A1 | 12/2013 | Stroot |
| 2014/0261213 A1 | 9/2014 | Stiles, Jr. et al. |
| 2014/0293040 A1 | 10/2014 | Hietaniemi |
| 2015/0167045 A1 | 6/2015 | Brubacher |
| 2015/0230439 A1 | 8/2015 | Harwood |
| 2015/0250113 A1 | 9/2015 | Shoham et al. |
| 2015/0256747 A1 | 9/2015 | Grotto et al. |
| 2015/0342161 A1 | 12/2015 | Sheriff |
| 2015/0347817 A1 | 12/2015 | Valvik et al. |
| 2015/0366173 A1 | 12/2015 | Myers |
| 2016/0356756 A1 | 12/2016 | Covi |
| 2017/0260546 A1 | 9/2017 | Qimron et al. |
| 2017/0299382 A1 | 10/2017 | Yang et al. |
| 2018/0125041 A1 | 5/2018 | Holm et al. |
| 2019/0008126 A1 | 1/2019 | Shishehchian |
| 2019/0071336 A1 | 3/2019 | Greenwald et al. |
| 2019/0082661 A1 | 3/2019 | Lahav et al. |
| 2019/0135393 A1 | 5/2019 | Pieterkosky |

(56) References Cited

U.S. PATENT DOCUMENTS

| | | |
|---|---|---|
| 2019/0141964 A1 | 5/2019 | Perslow et al. |
| 2019/0169046 A1 | 6/2019 | Holm |
| 2019/0200584 A1 | 7/2019 | Holm |
| 2020/0396970 A1 | 12/2020 | Holm et al. |
| 2021/0127646 A1 | 5/2021 | Holm |
| 2021/0137082 A1 | 5/2021 | Holm |
| 2021/0195874 A1 | 7/2021 | Holm et al. |
| 2021/0227807 A1 | 7/2021 | Holm et al. |
| 2021/0235010 A1 | 7/2021 | Wallace et al. |
| 2021/0274758 A1 | 9/2021 | Holm et al. |
| 2021/0275604 A1 | 9/2021 | Holm |
| 2021/0278378 A1 | 9/2021 | Holm |

FOREIGN PATENT DOCUMENTS

| | | |
|---|---|---|
| DM | 205963 | 3/2020 |
| GB | 2464686 | 4/2010 |
| JP | H01112935 | 5/1989 |
| WO | WO200241703 | 5/2002 |
| WO | WO2006042371 | 4/2006 |
| WO | WO2008094132 | 8/2008 |
| WO | WO2016154602 | 9/2016 |
| WO | WO2017002081 | 1/2017 |
| WO | WO2017153986 | 9/2017 |
| WO | WO2018184029 | 4/2018 |
| WO | WO2018169412 | 9/2018 |
| WO | WO2021150873 | 7/2021 |
| WO | WO2021162847 | 8/2021 |
| WO | WO2021178080 | 9/2021 |
| WO | WO2021178431 | 9/2021 |
| WO | WO2021216225 | 10/2021 |
| WO | WO2021221745 | 11/2021 |

OTHER PUBLICATIONS

Van Der Heile Tony et al., Composition, Treatment and Use of Saline Gorundwater for Aquaculture in the Netherlands, World Aquaculture, Jun. 2014, pp. 23-27, Nov. 2014.

Garcia-Bencochea, Jose I et al., Deep Well Disposal of Waste Waters in Saline Aquifers of South Florida, Abstract, American Geophysical Union Water Resources Research, Oct. 1970, 1 page, Oct. 1970.

Howard, Mark R., Down the Drain, Florida Trend, Jan. 1, 2000, hhttp://www.floridatrend.com/print/article/13274, 2 Pages, Jan. 1, 2000.

Gorman J. et al., Economic Feasibility of Utilizing West Alabama Saline Ground Water to Produce Florida Pompano and Hybrid Striped Bass in a Recirculating Aquaculture System, Alabama Agricultural Experiment Station, Auburn University, 19 Pages, Dec. 1, 2009.

Sharrer, Mark J. et al. Evaluation of Geotextile Filtration Applying Coagulant and Flocculant Amendments for Aquaculture, biosolids dewatering and phosphorus removal, Aquacultural Engineering, vol. 40, Issue 1, Jan. 2009, 10 Pages, <URL:https://www.sciencedirect.com/science/article/pii/S0144860908000678> (Accessed Dec. 4, 2017), Jan. 1, 2009.

Haberfeld, Joseph, Letter RE First Request for Additional Information (RAI), Florida Department of Environmental Protection, 6 pages, Jun. 4, 2013.

Storro, Gaute, Investigations of Salt groundwater at Akvaforsk Research Institute, Sunndalsora, Norway, Geological Survey of Norway, NGU-rapport 93.029, 1993, 11 pages, Jan. 1, 1993.

Milchman, Jon, Construction Clearance Permit Application, Florida Department of Environmental Protection, (FDEP), 5 pages, May 12, 2013.

Sun Min et al., Models for estimating feed intake in aquaculture, a review, abstract, Computers and Electornics in Agriculture, vol. 127, <URL:http://www.sciencedirect.com/science/article/pii/S0168169916304240> (Accessed Dec. 4, 2017), 4 pages, Sep. 2016.

South Dade News Leader, Homestead, Notice of Draft Pemit, Miade-Dade County, Florida, Sep. 13, 2013, 1 Page, Sep. 13, 2013.

South Dade News Leader, Notice of Intent, Homestead , Miade-Dade County, Florida, Oct. 18, 2013, 1 page, Oct. 18, 2013.

Florida Department of Environmental Protection, Notice of Permit, 8 pages, Nov. 4, 2013.

Lindholm-Lehto et al., Depuration of Geosmin and 2 mehtylisoborneol-induced off-flavors in recirculation aquacultre system (RAS) farmed European whitefish coregonus lavaretus, Jul. 10, 2019.

Sompong et al., Microbial Degradation of musty odor in aquaculture pond, International Journal of Agricultural Technology, Dec. 1, 2018.

Tucker et al., Managing Off-Flavor Problems in Pond-Raised Catfish, SRAC Publication, Oct. 5, 2018.

Small, Brian et al., On the Feasibility of Establishing a Saline Aquaculture Industry in Illinois, Illinois Sustainable Technology Center [online] <URL:http://www.istc.illinois.edu/info/library_docs/TR/TR051.pdf>, 46 Pages, Mar. 2014.

Akva Group, Recirculation Systems, 6 pages, <URL:http://www.akvagroup.com/products/land-based-aquaculture/recirculation systems> (Accessed Dec. 4, 2017).

State of Florida, Well Completion Report, Feb. 2015, 23 Pages, Feb. 2015.

Water Source, University of Alaska, Fairbanks, School of Fisheries & Ocean Sciences, 53 Pages, <URL:hhttps://www.sfos.uaf.edu/fitc/teaching/courses/fish336/materials/FISH%20336%20Letc%2031%20Water%20Quality%203.pdf> (Accessed), Dec. 4, 2017.

Hoefel et al., Cooperative biodegradation of geosmin by a consortium comprising three gram-negative bacteria isolated from the biofilm of a sand filter column. Letters in Applied Microbiology, 43, pp. 417-423, Jan. 1, 2006.

Mcdowall et al., Enhancing biofiltration of geosmin by seeding sand filter cols. with a consortium of geosmin degrading bacteria. Water Research, 43, pp. 433-440, Jan. 1, 2009.

Almeida et al., Almeida et al. (Antibiotics, 2019; 8: 192), Oct. 24, 2019.

Guttman et al., Guttman et al. (Aquaculture, 2008; 279; 85-91), Mar. 26, 2008.

* cited by examiner

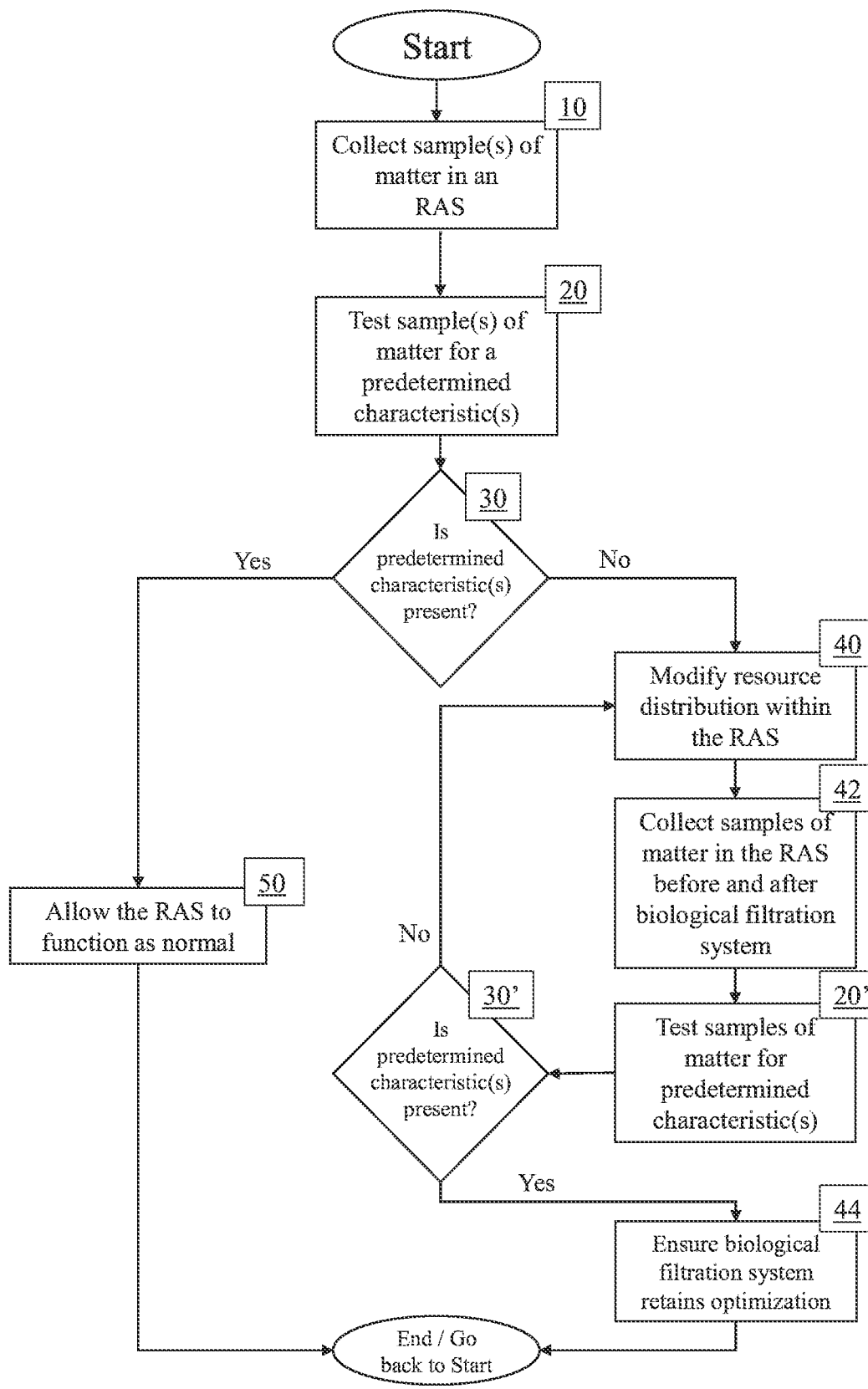

METHOD FOR OPTIMIZATION OF FILTRATION IN AN AQUACULTURE SYSTEM

CLAIM OF PRIORITY

This application is a Continuation of U.S. application Ser. No. 17/079,007, which was filed on Oct. 23, 2020, and which is a Continuation-in-Part of U.S. Patent having Ser. No. 16/992,865, which was filed on Aug. 13, 2020, which is a Continuation-in-Part of U.S. Patent having Ser. No. 16/992,760, which was filed on Aug. 13, 2020, which is a Continuation-in-Part of U.S. Patent having Ser. No. 16/991,162, which was filed on Aug. 12, 2020, which claims benefit to a U.S. Provisional Patent Application having Ser. No. 62/985,592, filed on Mar. 5, 2020. Each of the above applications are incorporated by reference herein in their entirety.

BACKGROUND OF THE INVENTION

Field of the Invention

The present invention relates generally to utilizing an aquaculture system, or more specifically, a recirculating aquaculture system (RAS) for farming aquaculture, with at least one filter. Further, the present invention relates to a method for optimizing and controlling at least one filter and/or filtration system utilized by an RAS. Specifically, the present invention relates to optimizing and controlling biological filtration systems utilized by an RAS so as to ensure consistency of resources within the RAS over time.

Description of the Related Art

At the present day, a recirculating aquaculture system(s) (RAS) is/are commonly used in the aquaculture farming industry. Essentially, an RAS provides an aquaculture farming production a means for a financially favorable production method, at least through limiting water consumption for use in farming. RAS's have proven to be highly effective in the art of aquaculture farming and are being adopted all over the world. Although RAS's are generally well received by the industry, when used, complications in water quality and/or characteristics thereof may emerge. These complications range from nutrient imbalances within the water, production of harmful compounds and/or living organisms within the water, and/or aquaculture developing diseases, non-natural flavor profiles, and/or perishing from exposure to such water. Such complications are believed to be caused at least by at least one non-optimized filter and/or filtration system an RAS utilizes in order to function. Specifically, these complications are believed to be exacerbated at least by at least one non-optimized biological filter and/or biological filtration system an RAS utilizes. A biological filter and/or biological filtration system may be defined as at least one filtration device which comprises at least one form of bacteria in order to filter a material and/or fluid. For purposes of this present invention, a biological filter and/or biological filtration system will be referenced, in non-limiting form, either in singularity or plural form, as a biological filtration system. Also, for purposes of this present invention, "non-optimized" may be defined as inconsistent, ineffective, or volatile. As should now be apparent, such complications are believed to be caused at least by a non-optimized biological filtration system, meaning such systems may have specific characteristics subject to volatility, inconsistencies and/or may become ineffective entirely. Evidence for the above mentioned beliefs are at least found in sampling at least one resource located within a portion of the RAS, discovering one above referenced complication within the sample(s), and observing imbalances within the RAS's biological filtration system.

As should be apparent, the above referenced complications create a financial strain on an aquaculture farming production experiencing the complications. The product (aquaculture) is exposed to water with complications, and as previously mentioned, diseases proliferate, non-natural flavor profiles are present, and/or aquaculture perish. Each of these issues detract from the profitability of an aquaculture farming production and as such, a solution is vital to operations of such an aquaculture farming production. It becomes apparent that these complications are becoming more prevalent in RAS's and plausibly, are known to be caused at least by at least one non-optimized filter and/or filtration system. More specifically, it becomes apparent that these complications are becoming more prevalent in RAS's and plausibly, are known to be caused at least by a non-optimized biological filtration system.

SUMMARY OF THE INVENTION

In view of the foregoing disadvantages inherent in recirculating aquaculture systems now present today, the present invention provides a new method for optimization of filtration in an aquaculture system.

The general purpose of the present invention, which will be described subsequently in greater detail, is to provide a new method for optimization of filtration in an aquaculture system of which many novel features are a result, which are not anticipated, rendered obvious, suggested, or even implied by any of the prior art of aquaculture systems in combination or singularity thereof.

Thus, the present invention is directed to a method to optimize a filtration system, which may be a biological filtration system, in an aquaculture system, and more specifically, a recirculating aquaculture system (RAS). As previously disclosed, a biological filtration system may comprise/be defined by at least one biological filter and/or at least one biological filtration system. In one or multiple embodiments of the present invention, the present invention may function and/or have enhanced functionality while in direct or indirect conjunction with innovative methods for compound detection and mitigation in aquaculture systems, aquaculture system sensor arrays, or methods thereof as will be subsequently described. In contrast, in one or multiple embodiments of the present invention, the present invention may function in an aquaculture system with at least a filtration system, which may comprise at least one filter, in absence of the previously mentioned innovative methods, sensor arrays and/or methods thereof.

The method to optimize a filtration system in an aquaculture system may include, but not be limited to, collecting at least one sample of matter within an RAS, testing the sample(s) for at least one predetermined characteristic, determining if such predetermined characteristic(s) of the sample(s) is/are present, then (1) if not, modify resource distribution within the RAS so as to optimize a biological filtration system located within the RAS, collect at least two samples of matter in the RAS, which may be in locations before and after the biological filtration system located within the RAS, and test such samples of matter for at least one predetermined characteristic, then (a) if not present, revert back until (1), or (b) if present, ensure the biological filtration system retains a state of optimization, or (2) if so, allow the RAS to continue operating as normal.

As previously described, the aquaculture system having the method applied thereto may be a recirculating aquaculture system. The RAS may contain at least one interworking of which could be, but not be limited to, fish tanks, temperature sensors, oxygen sensors, mechanical filters, discharge pumps, backwash pumps, level sensors, reservoirs, pH sensors, pumps, lime dosing units, biological filters, namely, fixed bed biological filters, moving bed biological filters, ceramic ring filters, ceramic ball filters, biological ball filters, filter flosses, sponge filters, and ceramic noodle filters. Further, the at least one RAS interworking could be, but not be limited to, trickle filters, oxygen cones, UV filters, wastewater injection systems, sludge tanks, flocculation tanks, drill strings, hatcheries, pump sumps, denitrification filters, fries and pans, sludge concentration filters, post smolt tanks, and/or on growing tanks.

As an RAS may comprise a multitude of interworkings, one embodiment of the present invention may have at least one biological filter (of any type as disclosed and/or undisclosed above), which if in singularity or in connection with other biological filters, may be referred to as a biological filtration system. Multiple biological filtration systems may exist on/within an RAS, each comprising locations pertinent towards different stages of aquaculture development. Such a biological filtration system, by virtue of fluid communication, may be positioned in-between two separate RAS interworkings. To further this concept, by way of non-limiting example, one interworking of the RAS may be located in a first position, be in fluid communication with a biological filtration system, for example, at an input to the biological filtration system, then, for example, at an output to the biological filtration system, have a separate interworking of the RAS located in a second position, and be in fluid communication thereto.

As should be inherent, the RAS may be structured to contain, grow, and/or otherwise farm aquaculture. The aquaculture may be, but not be limited to, shrimp, lobster, scallops, salmon, tuna, sea bass, halibut, cod, jack, octopus, anchovies, crab, marlin, swordfish, mahi mahi, porgy, snapper, hog fish, ballyhoo, catfish, trout, eel, flounder, herring, tilapia, sturgeon, pikeperch, whitefish, carp, haddock, mullet, and/or mackerel.

The method to optimize a filtration system in an aquaculture system may be applied at any time to an RAS. This may include, but not be limited to, having the RAS operating without aquaculture, having the RAS operating with aquaculture, and/or having the RAS un-operational. In the event that the present invention is applied to an un-operational RAS, the RAS may have been previously operational, in order to accumulate materials/resources to sample, such as, but not limited to sludge, and/or residual water. Also, in the event that the present invention is applied to an unoperational RAS, the inventive methodology, in some embodiments may be applied after a period of time until the RAS has become operational again. The inventive methodology may also be carried out by a user, wherein such a user may be, but not be limited to, a human operator, a robotic operator, a computational machine, which may or may not utilize automated means, and/or a combination thereof. Further, as many biological filtration systems may exist on/within one RAS, the inventive methodology may be applied to all such biological filtration systems simultaneously, or on a case by case basis, including grouping some biological filtration systems together per purposes of conducting the inventive methodology.

The at least one sample of matter collected in an RAS per the inventive methodology may be, but not be limited to, water, aquaculture feed post-introduction into the RAS, a fluid, aquaculture tissue, sludge, algae, common products or byproducts commonly found in RAS's, and/or a combination thereof. As should be apparent, multiple samples of matter may be collected, at any point located within an RAS. Further, the at least one sample of matter may be tested for at least one predetermined characteristic. Testing may be completed via a multitude of different means, which will be subsequently described. Such a predetermined characteristic(s) may be defined as quantifiable or index-able value(s) a user may be testing for. Examples of a predetermined characteristic(s) may be, but not be limited to, salinity, salinity levels, composition of fish feed, water particle concentration, water particle concentration levels, water nitrite levels, water nitrate levels, water ammonia levels, water ammonium levels, the presence and/or concentrations of living organism and/or measureable levels of compounds within water, including volume percentages thereof, in relation to water. As should be apparent, a user may elect to test at least one sample of matter for multiple predetermined characteristics or alternatively, a user may elect to test multiple samples of matter for one or multiple predetermine characteristics.

As a user may be attempting to determine if at least one predetermined characteristic is present in at least one sample of matter, in accordance with the present invention, a user may wish to define such at least one predetermined characteristic prior to carrying out the inventive methodology. By way of non-limiting example, a user may wish to define a certain range of quantifiable values to pertain to such a predetermined characteristic per a sample. Multiple ranges for multiple predetermined characteristics may also be defined. Continuing the non-limiting example, a user may wish to define a range of water nitrate levels, and thereby will be able to determine if this range is present within the testing of the sample. In one embodiment, a user may define at least one quantifiable or index-able value as a predetermined characteristic. Such an at least one predetermined characteristic may be known to produce conditions for optimizing biological filtration systems within the RAS.

In determination of at least one predetermined characteristic being present (or conversely, not present), a user may then elect to carry out two different procedures per the inventive methodology. In the event that a user determines at least one predetermined characteristic is present, and/or the user determines the presence of predetermined characteristics, which may be considered to be satisfactory, a user may elect to allow the RAS to continuing operating as normal. If a user elects to allow an RAS to continue operating as normal, this may comprise having a user carry out standard operating procedures on an RAS, depending on the status of the RAS (functioning, sitting idle, or other statuses known to one skilled in the art of recirculating aquaculture systems). Following this procedure, a user may then end the inventive methodology, or re-start the methodology.

In the event that a user determines at least one predetermined characteristic is not present, and/or the user determines the presence of predetermined characteristics is considered to be unsatisfactory, a user may first elect to modify resource distribution within the RAS. The modification of resource distribution may be defined as, but not be limited to, controlling, altering, and/or otherwise monitoring the introduction and/or distribution of resources that enter or otherwise exist within an RAS. Such resources may be, but not be limited to, water, fish feed, substances, living organisms and quantifiable properties thereof. By way of non-limiting example, a user may wish to modify resource distribution within the RAS via controlling and/or selecting the chemical composition of aquaculture feed that enters the RAS, and/or the rate by which the aquaculture feed does so. In such a case, the chemical composition of aquaculture feed that enters the RAS may be considered a resource. In one embodiment, a user may wish to modify resource distribution at a location, in fluid communication with and before an RAS's prospective biological filtration system. In any event, by way of non-limiting example, a user may indicate and/or record the actions taken, resources altered, resources selected, and/or quantifiable/index-able values experimented on in order to modify resource distribution. Such indication and/or recordation may be recorded by mental note, pen and paper, computer table entry and/or by automated means. A user may modify resource distribution within the RAS so as to influence biological filtration systems to operate at a desired level. In one embodiment of the present invention, a user may modify resource distribution within the RAS so as to influence biological filtration systems to operate at an optimized level. An optimized level, in the context of filtration within an RAS may be a quantifiable/index-able/measureable/observable level a user is attempting to reach, at the sole discretion of the user.

Upon a user modifying resource distribution within the RAS, so as to influence biological filtration systems to operate at a desired/optimized level, a user may wish to the collect at least two samples of matter in the RAS. Such samples may be taken at a location before, and at a location after a prospective RAS's biological filtration system. The samples taken may be in accordance with the procedure of sampling as previously disclosed, although, in this procedure of the inventive methodology, at least two samples will be taken, which may be taken at specified locations.

Next, the at least two samples may be tested for at least one predetermined characteristic. This procedure of testing may be in accordance with the procedure of testing as previously disclosed, or as will be subsequently described. In this procedure of the inventive methodology, as least two samples will be tested and as such, the method of testing may or may not be different. Further, the at least two samples may comprise different samples of matter. After testing, a user may once again determine if at least one predetermined characteristic is present. Such a determination as to if a predetermined characteristic(s) is/are present may be in accordance with disclosure on predetermined characteristics as previously mentioned. In one embodiment of the present invention, predetermined characteristics may change throughout the inventive methodology. In order to illustrate this, by way of non-limiting example, in a first procedure of the inventive methodology, a user may select and/or specify a first predetermined characteristic(s), such as, but not limited to, a nitrate level, then in a second portion, of the inventive methodology, after at least some time passing, a user may select and/or specify a second predetermined characteristic(s), such as, but not limited to, an ammonium level.

A user may then, once again determine if at least one predetermined characteristic is present in the at least two samples tested and/or the user may determine if predetermined characteristics are considered to be satisfactory or unsatisfactory in the at least two samples tested. The determination, as made by a user may be in accordance with the determination of if a predetermined characteristic is present and/or satisfactory/unsatisfactory, as previously mentioned.

In the event that a user determines a predetermined characteristic(s) is/are not present, or unsatisfactory, the user may elect to go back to the procedure of modifying a resource distribution within the RAS, as previously disclosed, and continue the inventive methodology from that procedure. In the event that a user determines that a predetermined characteristic(s) is/are present or satisfactory, then a user may elect to ensure the biological filtration system retains a state of optimization.

Following the procedure above, as a user may elect to ensure the biological filtration system retains a state of optimization, wherein a multitude of embodiments may exist in order to ensure the biological filtration system retains a state of optimization. In all embodiments, a user may at least reference previously indicated and/or recorded actions taken, resources altered, resources selected, and/or quantifiable/index-able values experimented on in order to modify resource distribution, as previously mentioned. A user may reference the mentioned factors in order to understand the actions taken, resources altered, resources selected and/or quantifiable/index-able values so as to utilize such an understanding, to discern the most effective route to ensure the biological filtration system retains a state of optimization. As should be apparent, the procedure of ensuring the biological filtration system retains a state of optimization entails a user discerning an effective route to ensure the biological filtration system retains a state of optimization, and the user acting on such a discernment. In at least one embodiment, a user acting on such a discernment may entail, but not be limited to, a user taking actions, altering resources, selecting resources and/or leveraging quantifiable/index-able values in order to influence at least a portion of the RAS, thereby ensuring the biological filtration system retains a state of optimization. In one embodiment, a user may act on such a discernment by allowing the RAS to continue operating as normal. Upon completion of the procedure wherein a user ensures the biological filtration system retains a state of optimization, a user may end the inventive methodology and/or restart the inventive methodology.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a flowchart illustrating the overall process of the present invention of a method for optimization of filtration in an aquaculture system.

Like reference numerals refer to like parts throughout the several views of the drawings.

DETAILED DESCRIPTION OF THE PREFERRED EMBODIMENT

Turning now descriptively to the figures, FIG. 1 illustrates an inventive method for optimizing and controlling at least one filter and/or filtration system utilized by an aquaculture system from the standpoint of a general overview. The aquaculture system can be, and will be, referred to as a recirculating aquaculture system (RAS). The at least one filter and/or filtration system can be at least one biological filter and/or biological filtration system. In either embodiment, the at least one filter and/or filtration system will be referred to as a biological filtration system.

FIG. 1 may encompass a starting point for the present inventive methodology and may imply a location and/or locations within an RAS for at least one sample of matter to be taken. In one embodiment, this may encompass the beginning of the inventive methodology by collecting at least one sample of matter in an RAS 10. As previously stated, the inventive methodology may be enhanced via utilization of other methodologies, but is not required. A user may choose a single location or multiple locations within an RAS to carry out collecting at least one sample of matter 10. A user may be defined as, but not limited to an individual, group, team, automated computer system, or robot. A user may subsequently complete procedure 10 and procedures that follow. Within procedure 10, a user may choose to indicate and/or record which location or locations of a respective RAS that has/have been selected to carry out taking at least one sample. Indication and/or recording of which location or locations of the RAS that had been selected may be recorded by mental note, pen and paper, computer table entry, or by automated means.

Further, procedure 10 may be carried out by collecting one sample of matter or multiple, wherein the user may then indicate properties of the sample or samples of matter, such as, but not limited to, the time and date in which the sample or samples was/were taken, what the contents of the sample or samples is/are, mass or masses of the sample or samples, and/or other basic quantifiable properties of the sample or samples. The sample or samples may also be taken at a location or locations designated to different stages of aquaculture development, which, by non-limiting example, may have a sample taken at a portion of the aquaculture system designated to hold aquaculture at one week since birth, and another sample is taken at a portion of the aquaculture system designated to hold aquaculture at three weeks since birth. By way of another non-limiting example, if multiple samples are taken, a user may choose to take an individual sample, or multiple samples at one point in time, and then may choose to take an individual sample, or multiple samples at another point in time. Also, the sample or samples may be taken at a location or locations with specific positioning in relation to the biological filtration system, wherein such a location or locations may be determined by a user.

By way of non-limiting, continuous example, one embodiment of procedure 10 may encompass a user collecting a sample of water within an RAS, at a location that is located after an outlet to a biological filtration system. A user may collect this sample of water by placing the sampled water in a plastic, sterile vile. A user may then record quantifiable and/or index-able characteristics of sample, such as, but not limited to the sample's volume, density and/or specific gravity.

Upon completion of procedure 10, the user may then test the at least one sample of matter for at least one predetermined characteristic 20. Testing may take place via a plethora of different means and will subsequently described. Also, a predetermined characteristic may take one or multiple different forms. Further, a predetermined characteristic may encompass one or more quantifiable and/or index-able values(s), as was previously described. Continuing the non-limiting example as described above, a user may elect to set predetermined characteristics as nitrate and ammonium levels of the sample of water taken. In such an example, a range for such predetermined characteristics may be set. Ranges, for example may be, ammonium levels from 0.001 mg/L to 0.02 mg/L and nitrate levels of 0 mg/L to 20 mg/L.

Within procedure 20, testing may also take one or multiple different forms. Also, as one or multiple samples can be taken, within procedure 20, multiple tests may be conducted on one or multiple samples of matter. Testing may include, but not be limited to, stir bar sorptive extraction, gas chromatography-mass spectrometry, statistical analyses, DNA sequencing and/or identification of microbiota, pH testing, fine particle per a unit over volume testing, test tube testing, salinity metering, testing for concentrations of chemicals, compounds, elements and/or substances and/or a series of combinations thereof.

As such, and continuing the non-limiting example as above, a user may utilize testing for concentrations of ammonium levels and nitrate levels within the sample of water taken from the RAS. Such testing may take place via dilution of the sample of water with a chemical activator, and comparing the diluted water to a test strip.

Upon a user completing procedure 20, a user may then realize if a predetermined characteristic(s) is present 30. As should be apparent, a user may determine if a predetermined characteristic(s) is present via the results of testing from procedure 20. A user may compare the results of testing to determine if the sample or samples of matter either have, or do not have the predetermined characteristic(s) as set by a user. As multiple predetermined characteristics may be set, many tests conducted, and many samples taken, a user may elect to determine, in procedure 30 if collectively, predetermined characteristics are satisfactorily present or unsatisfactorily present. In the event that predetermined characteristics are satisfactorily present, the majority of predetermined characteristics set may have been determined to be present by a user. In the event that predetermined characteristics are unsatisfactorily present, the majority of predetermined characteristics set may not have been determined to be present by a user. Predetermined characteristic presence may be derived from tables, biological libraries, safety limits and/or by sole discretion of a user.

Continuing the non-limiting example from above, a user may determine that the sample of matter collected in procedure 10, upon testing and specifying predetermined characteristics in procedure 20, has predetermined characteristics present, or found the predetermined characteristics to be satisfactorily present. Such a determination could be made by this example via the ammonium and nitrate levels having a measurement within the ranges (as previously mentioned) defined by the predetermined characteristics and/or a +/−0.005 mg/L error threshold present for ammonium and/or a +/−5 mg/L error threshold present for nitrate from the predetermined characteristic ranges. In this scenario, a user may allow the RAS to continue operating normally 50. Allowing an RAS to continue operating normally may be defined as described above. Following procedure 50, a user may end, or restart the inventive methodology.

Also, continuing the non-limiting example from above, a user may determine that the sample of water collected in procedure 10, upon testing and specifying predetermined characteristics in procedure 20, does not have predetermined characteristics present, or found the predetermined characteristics to be unsatisfactorily present. Such a determination could be made by this example via the ammonium and nitrate levels falling short of or exceeding the ranges (as previously mentioned) defined by the predetermined characteristics. In this scenario, a user may proceed to the procedure of modifying resource distribution within the RAS 40.

Modifying resource distribution within an RAS, as previously defined may be carried out in a plethora of different controlled forms. A user may realize how to modify resource distribution by viewing and/or accessing a data table with predetermined modifications to resource distribution in relation to non-present and/or unsatisfactory predetermined characteristic(s) presence. Such a data table, or other form of informational disclosure, may allow a user to realize how to obtain a desired result within the RAS from modification of resource distribution. Further, a user may have to perform experimentation in order to determine how to modify resource distribution within an RAS, in order to obtain a desired result from the modification of resource distribution. As should be apparent, a desired result of modifying resource distribution, and the inventive methodology as a whole, is to obtain an optimized biological filtration system within an RAS. Further, modifying resource distribution may encompass, beyond the previously mentioned, the controlling and/or selection of pro and/or pre biotics to be placed into the RAS, the controlling and/or selection of natural and/or engineered bacteriophages to be placed into the RAS, controlling and/or selection of chemicals, compounds, elements and/or substances to be placed into the RAS. Each may be defined as a resource.

As part of procedure 40, upon a user realizing the modifications to be made to resource distribution within an RAS, a user may act on such a realization. As previously mentioned, such an acting on a realization may be carried out via, but not be limited to, controlling, altering, and/or otherwise monitoring the introduction and/or distribution of resources that enter or otherwise exist within an RAS. In one embodiment, a user may control the amount of a resource entering the RAS in a first location of the RAS, then alter the distribution of a resource located within a second location of the RAS. Following, a user may complete procedure 40.

In order to illustrate an embodiment, in continuing the example as continuously mentioned, upon a user determining a sample of water does not have predetermined characteristics present, or such characteristics are unsatisfactorily present, a user may reference a table in order to understand what resources (and their distributions) must be modified in relation to the non-present predetermined characteristic(s). Such an action being carried out to achieve the desired outcome of optimization of biological filtration within the prospective RAS. Upon referencing a table, a user may then act on the realization of what resources (and their distributions) must be modified, via controlling, altering and/or otherwise monitoring the introduction and/or distribution of such resources that may enter or otherwise exist within an RAS. A user may add additional resources, such as liquid ammonia at a first location of an RAS. Further, a user may add additional resources, such as pelletized nitrite to a second location of an RAS.

Following procedure 40, a user may or may not allow a predetermine period of time to pass by, then collect samples of matter in the RAS at locations before and after the biological filtration system 42. Per procedure 42, a user may collect at least two samples of matter. In an embodiment wherein two samples of matter are taken, as previously mentioned, such samples be taken at different locations within an RAS. In the embodiment wherein two samples are taken, one sample may be taken at a first location, which may be at an interworking of an RAS that is located, in communication, before an inlet to the biological filtration system. Also in such an embodiment, another sample may be taken at a second location, which may be at an interworking of an RAS that is located, in communication, following an outlet to the biological filtration system. Each such sample in the embodiment, or in other embodiments wherein at least two samples are taken per procedure 42, may be sampled per procedure 10, as described above.

By virtue of the continuous non-limiting example, upon a user completing procedure 40 as described above and allowing a predetermined period of time to pass by, a user may then collect two New samples of water, at two distinct locations within an RAS. The locations and details regarding the samples, may be quantified and/or indexed for later use.

Following procedure 42, a user may then test the at least two samples obtained from procedure 42 for a predetermined characteristic(s) 20'. Such testing may take place via testing as previously described. The predetermined characteristic(s), on part of procedure 20', may also be defined and/or realized via as previously described as well. Within procedure 20', at least two samples of matter may be tested, which may occur in many different forms, and not be limited to one forum of testing.

Also, by virtue of the continuous non-limiting example, upon a user completing procedure 42 as described above, a user may test the two samples of water. A user may utilize testing for concentrations of both ammonium levels and nitrate levels within each sample of water taken from the RAS. Such testing may take place via dilution of the samples of water with a chemical activator and comparing the diluted water to a test strip.

Upon completion of procedure 20', a user may determine if predetermined characteristic(s) of the tested at least two samples is/are present 30'. Such a determination may be made via as previously described. A user may be attempting to determine if an RAS, and more specifically an RAS's biological filtration system has obtained a desired result from modification of resource distribution 40. Again, such a desired result may be an optimized biological filtration system. Also as previously mentioned, a user may determine if a predetermined characteristic(s) is/are satisfactorily present, or non-satisfactorily present. As such, once a determination is made, a user will select between two routes in order to complete the inventive methodology. In the event that a user determined the predetermined characteristic(s) is/are not present, or is/are non-satisfactorily present, a user may elect to follow the "No" track, as shown in FIG. 1, leading back to procedure 40 and continue the inventive methodology within the loop defined within the figure, until a "Yes" track can be followed. In the even that a user determined the predetermined characteristic(s) is/are present, or is/are satisfactorily present, a user may elect to follow the "Yes" track. In such an event, a user will complete procedure 30' and ensure the biological filtration system retains optimization 44.

By way of continuous non-limiting example, upon a user testing the samples of water and determining the results of the testing to have unsatisfactory levels of predetermined characteristics (wherein the results are not present), where ammonium and/or nitrate levels are not within the previously defined ranges and/or error limits, a user may elect to re-attempt to modify resource distribution within the RAS. Alternatively, upon a user testing the samples of water and determining the results of the testing to have satisfactory levels of predetermined characteristics (where in the results are present), where ammonium and/or nitrate levels are within the previously defined ranges and/or error limits, a user may continue the inventive methodology under procedure 44.

As should be apparent, upon a user modifying resource distribution within the RAS 40, collecting samples of matter within the RAS at specified locations 42, testing such samples for predetermined characteristic(s) 20' and identifying the fact that such predetermined condition(s) is/are present 30', a user may have optimized the biological filtration system with the RAS. As such, per the inventive methodology, a user may ensure the biological filtration system retains optimization 44. A multitude of embodiments may exist in order to ensure the biological filtration system retains a state of optimization. As previously discussed, a user may reference previously indicated and/or recorded actions taken, resources altered, resources selected and/or quantifiable/indexed values experimented on in order to modify resource distribution and act on such references. Further, a user may alter the standard operating procedures of the RAS in order to include new, modified and/or re-instated alterations so as to ensure the biological filtration system retains a state of optimization. Further yet, a user may not have to alter the RAS in any way, or the resource distribution thereof, as the previous modification of resource distribution (procedure 40) may have successfully optimized the biological filtration system to a point where no further modifications are needed. Following the completion of procedure 44, a user may end, or restart the inventive methodology.

To conclude the continuous example, a user may ensure biological filtration system retains optimization after determining, in procedure 30' that the results of the testing had satisfactory levels of predetermined characteristics of ammonium and/or nitrate levels, by adding in liquid ammonia at predetermined time intervals within a first location of an RAS and adding in chemical nitrate liquid ammonia at a first location of an RAS. Further, a user may add additional resources, such as pelletized nitrite to a second location of an RAS.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method for optimizing a filtration system within an aquaculture system comprising:
    taking at least one sample of matter from at least one interworking of the aquaculture system;
    testing the at least one sample of matter to determine a nitrate level of the at least one sample of matter;
    determining if the nitrate level of the at least one sample of matter is below a predetermined threshold of 20 mg/L;
    modifying resource distribution within the aquaculture system if the nitrate level is below the predetermined threshold of 20 mg/L;
    after taking the at least one sample of matter, taking at least two samples of matter from at least two interworkings of the aquaculture system;
    testing the at least two samples of matter to determine an ammonium level in the at least two samples of matter;
    determining if the ammonium level of the at least two samples of matter is between 0.001 mg/L and 0.02 mg/L; and
    further modifying resource distribution within the aquaculture system if the ammonium level is outside the range of 0.001 mg/L to 0.02 mg/L.

2. The method of claim 1, wherein the aquaculture system is a recirculating aquaculture system.

3. The method of claim 1, wherein the at least one sample of matter is water held within the aquaculture system.

4. The method of claim 1, wherein taking the at least one sample of matter further comprises utilizing at least one sterile container so as to collect the at least one sample of matter.

5. The method of claim 1, wherein taking the at least one sample of matter further comprises recording quantifiable properties of the at least one sample of matter.

6. The method of claim 1, wherein modifying resource distribution within the aquaculture system further comprises adding at least one of pelletized nitrite and liquid ammonia to the aquaculture system.

7. The method of claim 1, wherein taking at least two samples of matter from at least two interworkings of the aquaculture system further comprises having the at least two interworkings located in fluid communication with the filtration system.

8. The method of claim 7, further comprising at least one of the two interworkings having a first location before an inlet to the filtration system.

9. The method of claim 7, further comprising at least one of the two interworkings having a second location after an outlet to the filtration system.

10. The method of claim 1, wherein the at least two samples of matter are water held within the aquaculture system.

11. The method of claim 1, wherein taking at least two samples of matter further comprises recording quantifiable properties of the at least two samples of matter.

12. The method of claim 1, further comprising the step of modification of standard operating procedures of the aquaculture system.

13. A method of optimizing a biological filtration system within a recirculating aquaculture system, the biological filtration system having both an inlet and an outlet, the method comprising:
    determining nitrate concentration in water at a first location after the outlet of the biological filtration system;
    modifying resource distribution within the recirculating aquaculture system based on a change in nitrate concentration to optimize the biological filtration system;
    determining ammonium concentrations both at the first location and at a second location before the inlet of the biological system; and
    modifying resource distribution within the recirculating aquaculture system based on a change in ammonium concentration to optimize the biological filtration system.

14. The method of claim 13 wherein modifying resource distribution within the recirculating aquaculture system in response to determining nitrate concentration further comprises introduction of at least one of probiotics, prebiotics, and bacteriophages into the recirculating aquaculture system.

15. The method of claim 13 wherein modifying resource distribution within the recirculating aquaculture system in response to determining nitrate concentration further comprises introduction of pelletized nitrite into the recirculating aquaculture system.

16. The method of claim 13 wherein modifying resource distribution within the recirculating aquaculture system in response to determining ammonium concentration further comprises introduction of at least one of probiotics, prebiotics, and bacteriophages into the recirculating aquaculture system.

17. The method of claim 13 wherein modifying resource distribution within the recirculating aquaculture system in response to determining ammonium concentration further comprises introduction of liquid ammonia into the recirculating aquaculture system.

18. The method of claim 13 further comprising the step of allowing a predetermined period of time to pass between the steps of determining nitrite concentration and determining ammonium concentrations.

19. The method of claim 13 further comprising the step of modifying a standard operating procedure.

* * * * *